(12) United States Patent
Beals

(10) Patent No.: US 10,482,995 B2
(45) Date of Patent: Nov. 19, 2019

(54) NUCLEIC ACID AMPLIFICATION SIGNAL ACQUISITION AND SIGNAL ANALYSIS

(71) Applicant: Thorne Diagnostics, Inc., Beverly, MA (US)

(72) Inventor: Thomas P. Beals, Acton, MA (US)

(73) Assignee: Thorne Diagnostics, Inc., Beverly, MA (US)

( * ) Notice: Subject to any disclaimer, the term of this patent is extended or adjusted under 35 U.S.C. 154(b) by 407 days.

(21) Appl. No.: 14/278,305

(22) Filed: May 15, 2014

(65) Prior Publication Data

US 2015/0254399 A1   Sep. 10, 2015

Related U.S. Application Data

(60) Provisional application No. 61/823,564, filed on May 15, 2013.

(51) Int. Cl.
*G16B 40/00* (2019.01)
*C12Q 1/68* (2018.01)
*G01N 33/487* (2006.01)

(52) U.S. Cl.
CPC ............... *G16B 40/00* (2019.02); *C12Q 1/68* (2013.01); *G01N 33/487* (2013.01)

(58) Field of Classification Search
None
See application file for complete search history.

(56) References Cited

U.S. PATENT DOCUMENTS

2006/0223098 A1   10/2006   Lane et al.
2012/0164652 A1   6/2012    Clemens et al.

FOREIGN PATENT DOCUMENTS

WO   2008/157689 A2   12/2008

OTHER PUBLICATIONS

ICycler iQ Real-Time PCR Detection System Instruction Manual (2004).*
Beals et al. BMC Mol Biol 11:94 Dec. 7, 2010 at http://www.biomedcentral.com/1471-2199/11/94.*
Vogelstein et al. "Digital PCR," Proc. Natl. Acad. Sci. Aug. 1, 1999 (Aug. 1, 1999), vol. 96, pp. 9236-9241, entire document.
International Search Report and Written Opinion dated Apr. 23, 2015 in International Application No. PCT/US2014/038103.
R. G. Rutledge: "Sigmoidal curve-fitting redefines quantitative real-time PCR with the prospective of developing automated high-throughput applications", Nucleic Acids Research, vol. 32, No. 22, Dec. 14, 2004 (Dec. 14, 2004), pp. e178-e178, XP055042716, ISSN: 0305-1048, DOI: 10.1093/nar/gnh177.
Wilhelm Jochen et al: "Validation of an algorithm for automatic quantification of nucleic acid copy numbers by real-time polymerase chain reaction", Analytical Biochemistry, Elsevier, Amsterdam, NL, vol. 317, No. 2, Jun. 15, 2003 (Jun. 15, 2003), pp. 218-225, XP002312097, ISSN: 0003-2697, DOI:10.1016/S0003-2697(03)00167-2.

* cited by examiner

*Primary Examiner* — Joseph Woitach
(74) *Attorney, Agent, or Firm* — Stroock & Stroock & Lavan LLP

(57) ABSTRACT

Methods and systems are disclosed herein for improvements in real-time data collection and real-time signal analysis for nucleic acid amplification reactions.

11 Claims, 7 Drawing Sheets

Specification includes a Sequence Listing.

SEQUENCE LISTING

```
<160> NUMBER OF SEQ ID NOS: 4

<210> SEQ ID NO 1
<211> LENGTH: 57
<212> TYPE: DNA
<213> ORGANISM: Homo sapiens

<400> SEQUENCE: 1
agagacatcg cctctgggct aataggacta cttctaatct gtaagagcag atccctg      57

<210> SEQ ID NO 2
<211> LENGTH: 96
<212> TYPE: DNA
<213> ORGANISM: Homo sapiens

<400> SEQUENCE: 2
gcctgtccag ggatctgctc ttacaatacg agaacacccg attgagagag tttggaagtg   60
taggcgtgaa gtccataaca catacctgta ttcctc                             96

<210> SEQ ID NO 3
<211> LENGTH: 18
<212> TYPE: DNA
<213> ORGANISM: Homo sapiens

<400> SEQUENCE: 3
atggacttca cgcctaca                                                 18
```

```
<210> SEQ ID NO 4
<211> LENGTH: 18
<212> TYPE: DNA
<213> ORGANISM: Homo sapiens

<400> SEQUENCE: 4
tgtattcctc gcctgtcc                                                      18
```

NUCLEIC ACID AMPLIFICATION SIGNAL ACQUISITION AND SIGNAL ANALYSIS

RELATED APPLICATIONS

This application claims the benefit of, and priority to, U.S. Provisional Application No. 61/823,564, filed May 15, 2013, which is incorporated herein by reference in its entirety.

BACKGROUND

Estimation of the amount of a substance in a sample, including failure to detect that substance, has utility in a variety of fields. For example, if the substance is a nucleic acid sequence that is diagnostic for a pathogenic organism, it may be useful to know that that particular nucleic acid sequence is undetectable in a sample, or that the quantity of those sequences is decreasing in response to medication. In genetic diagnostics, the estimation of the copy number of a genomic DNA sequence can be diagnostic for the duplication or deletion of a chromosome segment. For example, in fetal ploidy, determination for diagnosis of Downs syndrome can be performed by comparing the copy number of chromosome 21 diagnostic sequences to the copy number of sequences that are diagnostic for another somatic chromosome. Because accurate diagnosis requires distinguishing two copies from three copies of chromosome 21 sequences, accurate quantification of copy number differences is essential. Further examples may be drawn from epidemiology, ecology, or research applications in gene expression, as well as other fields.

In many cases, the substance of interest may be present in the sample in an amount that is too small to be measured directly. Improved methods for nucleic acid amplification signal acquisition and signal analysis, for example for determining small amounts of substances in a sample with higher confidence and/or greater efficiency as compared to existing methods, are needed.

SUMMARY

The present invention provides, in various embodiments, systems and methods for analyzing data obtained from a biochemical amplification reaction. In some embodiments, the amplification reaction is a continuous (i.e., non-cyclic) reaction, from which data (e.g., signal proportional to product accumulation rate) are periodically sampled. In preferred embodiments, the invention uses an amplification reaction for which there exists an explicit mathematical model of the amplification. In alternative embodiments, the invention provides for empirical analysis of amplification reactions for which no explicit rate model exists.

In one aspect, the invention comprises a computer-implemented method for determining a value representative of an initial condition of a sample, comprising receiving, by a computer having at least one central processing unit including at least one microprocessor configured to execute instructions stored on at least one non-transitory computer-readable medium, (signal, time) data from a biochemical amplification procedure amplifying the nucleic acid sequence, a sub-sequence of the nucleic acid sequence, or a complementary sequence of nucleic acid sequence, wherein the (signal, time) data comprises signals proportional to accumulated amplification products produced in the biochemical amplification procedure, repeatedly recorded at a frequency sufficient for statistically significant biochemical reaction rate determination.

In some embodiments, the method includes performing first processing, by the computer, of the (signal, time) data to determine whether amplification has occurred; when amplification is determined not to have occurred, ending the method; and when amplification is determined to have occurred, performing second processing, by the computer, of the (signal, time) data, identifying an initial point.

In some embodiments, the method includes performing third processing, by the computer, of the (signal, time) data, selecting a current region around the initial point, and fitting a model to the current region.

In some embodiments, the method includes performing fourth processing, by the computer, of the (signal, time) data, determining a first correlation coefficient for the current region; extending the current region by a predetermined step size; determining a second correlation coefficient for the extended region; and comparing the first correlation coefficient and the second correlation coefficient. In some embodiments, when a difference between the first correlation coefficient and the second correlation coefficient is within predetermined fit criteria, the method includes defining, by the computer, the extended region as the current region and repeating said extending. In some embodiments, when the difference between the first correlation coefficient and the second correlation coefficient is not within the predetermined fit criteria, the method includes defining, by the computer, the extended region as a selected data subset.

In some embodiments, the method includes determining, by the computer, values of predefined statistical measures for the data subset, including initial and final time points delimiting the data subset, number of data points contained in the data subset, and values for predefined parameters of the model. In some embodiments, the method includes storing, by the computer, the data subset and the statistical measures in a database comprising at least one non-transitory computer-readable medium.

In some embodiments, the method includes determining, by the computer, the value representative of the initial condition of the sample based on the values for the parameters of the model; and displaying to a user, by the computer, the value representative of the initial condition of the sample.

In some embodiments, the second processing comprises fitting a smoothing spline to the (signal, time) data, and the initial point is a first derivative maximum obtained from the fitted spline.

In some embodiments, the model is a linear model, and the statistical measures include a slope and a Y-intercept of the line.

In some embodiments, the first processing comprises dividing, by the computer, the (signal, time) data into multiple sub-segments of predetermined size; dividing, by the computer, each sub-segment equally into proximal signal data comprising earlier data points and distal signal data comprising later data points; and determining, by the computer, a segment ratio for each sub-segment by determining a sum of the distal signal data and a sum of the proximal signal data, and dividing the sum of the distal signal data by the sum of the proximal signal data.

In some embodiments, the first processing further comprises determining, by the computer, a maximum segment ratio, and dividing the (signal, time) data into a baseline segment and a plateau segment separated at the position of the maximum segment ratio; dividing, by the computer, the baseline segment and the plateau segment into proximal and distal halves, and determining a first mode comprising the statistical mode of the proximal half of the baseline segment and a second mode comprising the statistical mode of the distal half of the plateau segment; and determining reaction amplitude, comprising the difference between the first mode and the second mode. In some embodiments, when the amplitude is determined not to be greater than a predetermined threshold, the first processing further comprises determining, by the computer, that no amplification has occurred. In some embodiments, when the amplitude is determined to be greater than the predetermined threshold, the first processing further comprises determining, by the computer, that amplification has occurred.

In some embodiments, the predetermined segment size is based on at least one of the number of data points and data variance.

In some embodiments, the value representative of the initial condition of the sample is a value representative of an amount of the nucleic acid sequence in the sample. In some embodiments, the method is performed in replicate on a plurality of aliquots of the sample.

In some embodiments, the method performed in replicate further comprises: when amplification is determined to have occurred in at least one aliquot, and not to have occurred in at least one other aliquot, determining, by the computer, a ratio of number of aliquots with no amplification to number of aliquots with amplification; and determining, by the computer, the value representative of the amount of the nucleic acid sequence in the sample based on statistical analysis of the ratio.

In some embodiments, the method performed in replicate further comprises: when amplification is determined to have occurred in at least two aliquots, generating, by the computer, a tabular compilation of the values for the parameters of the model for each of the at least two aliquots, and determining, by the computer, the value representative of the amount of the nucleic acid sequence in each of the at least two aliquots, based on statistical analysis of values in the tabular compilation.

In some embodiments, the method performed in replicate further comprises: determining, by the computer, the value representative of the amount of the nucleic acid sequence in the sample using values determined from all the replicates.

In some embodiments, the nucleic acid sequence is bound to a non-nucleic acid molecule, and the method further comprises determining, by the computer, a value representative of an amount of the non-nucleic acid molecule in the sample based on the value representative of the amount of the nucleic acid sequence in the sample.

In some embodiments, the biochemical amplification procedure comprises two-primer ramified rolling circle amplification (RAM). In some embodiments, the biochemical amplification procedure comprises helicase-dependent amplification (HDA), recombinase polymerase amplification (RPA), rolling circle amplification (RCA), loop-mediated isothermal amplification (LAMP), nicking enzyme amplification reaction (NEAR), or self-sustained sequence replication (3SR).

In some embodiments, the method is performed on each of a plurality of samples wherein the biochemical amplification procedure is the same and one and or more experimental factors of the biochemical amplification procedure are systematically varied for process optimization.

In some embodiments, the invention comprises means for performing any of the methods described above.

Additional features and advantages of the present invention are described further below. This summary section is meant merely to illustrate certain features of the invention, and is not meant to limit the scope of the invention in any way. The failure to discuss a specific feature or embodiment of the invention, or the inclusion of one or more features in this summary section, should not be construed to limit the invention as claimed.

BRIEF DESCRIPTION OF THE DRAWINGS

The foregoing summary, as well as the following detailed description of the preferred embodiments of the application, will be better understood when read in conjunction with the appended drawings. For the purposes of illustrating the methods of the present application, there are shown in the drawings preferred embodiments. It should be understood, however, that the application is not limited to the precise arrangements and instrumentalities shown. In the drawings:

FIG. 1A shows exemplary signal vs. cycle data from a PCR reaction. The horizontal axis records the count of thermal cycles; the vertical axis records a signal that is proportional to the reaction's cumulative amplification. One data point (shown as solid circles) was obtained for each thermal cycle. The graphic data points are connected by a line generated by a smoothing spline fitted to the data. The baseline region and the plateau are labeled.

FIG. 1B shows exemplary signal vs. time data from a RAM reaction. The horizontal axis records the elapsed reaction time in minutes; the vertical axis records a signal that is proportional to the reaction's cumulative amplification. One data point (shown as open circles) was obtained at three to five-second intervals. The graphic data points are connected by a line generated by a smoothing spline fitted to the data. The baseline region and the plateau are labeled.

FIG. 1C shows the data of FIG. 1A, transformed such that the vertical axis records a signal that is proportional to the logarithm of the reaction's cumulative amplification. An arrowed point is the maximum first derivative of the smoothing spline.

FIG. 1D shows the data of FIG. 1B, transformed such that the vertical axis records a signal that is proportional to the logarithm of the reaction's cumulative amplification. An arrowed point is the maximum first derivative of the smoothing spline.

FIG. 5A shows three higher-concentration samples, and FIG. 5B shows those three samples after ideal dilution. FIG. 5C illustrates ideal exponential amplification product accumulation over time, and FIG. 5D shows a logarithmic transformation of FIG. 5C. FIG. 5E superimposes idealized real-time amplification data on the amplification traces of FIG. 5D, and FIG. 5F represents the slopes and intercepts of FIG. 5E on a slope, intercept plot. FIG. 5G illustrates how statistical error would alter the slopes and intercepts of data from FIG. 5E, and FIG. 5H illustrates how the statistical error illustrated in FIG. 5G would appear if plotted as in FIG. 5F.

FIG. 6A shows a collection of 44 points, chosen by the procedure shown in FIG. 2, from the amplification data shown in FIG. 1D. Filled circles represent [time, log(signal)] data points. The line intersecting the data points was fitted to the collected points by linear regression.

FIG. 6B shows a subset of the data points from FIG. 1D, without initial points from the baseline and without terminal points from the plateau. The line through the data points and extending to the horizontal axis was plotted using the slope and intercept of the regression line shown in FIG. 6A.

FIG. 6C shows the data from FIG. 1D, without terminal points from the plateau, and with the vertical axis extended to form a figure similar to a single data-trace of FIG. 5E. The line through the data points and extending to the vertical axis, like the line shown in FIG. 6B, was plotted using the slope and intercept of the regression line shown in FIG. 6A.

FIG. 6D shows the data from FIG. 6C, adding three similarly-determined regression lines determined from reactions that are replicate reactions to the reaction that was the source of the data shown in FIG. 1D. The resulting figure resembles the outcome anticipated as shown in FIG. 5G.

FIG. 7A shows slope, intercept pairs from the most dilute template sample. Points identified by quality control standards are lightly circled. FIG. 7B shows data points from the same dilution that pass a data-quality metric. Dashed lines in FIG. 7B are aligned parallel to the apparent negative-sloped cluster of data-points.

FIG. 7C shows slope, intercept pairs from a less dilute template sample that was still expected to include some failures to amplify due to absence of template (Poisson failure). Points identified by quality control standards are lightly circled. FIG. 7D shows data points from the same dilution that pass a data-quality metric. Dashed lines in FIG. 7D are aligned parallel to the apparent negative-sloped cluster of data-points.

DETAILED DESCRIPTION

Figure 1A:
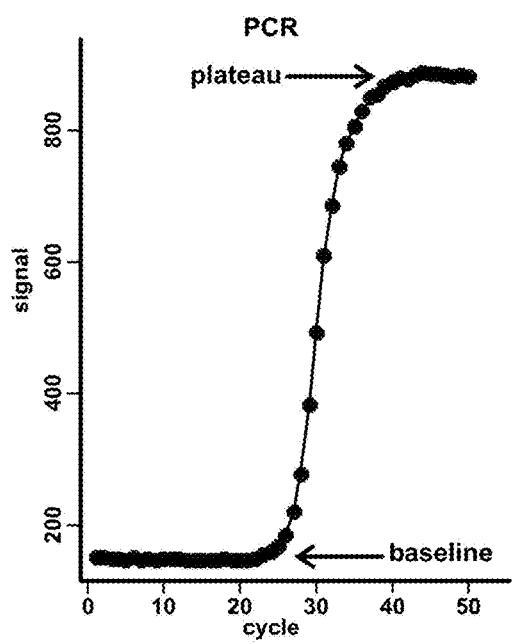
FIGS. 1A-D show graphic displays of (cycle, signal) data pairs for a polymerase chain reaction (PCR) and displays of (time, signal) data pairs for a two-primer ramified rolling circle (RAM) reaction.

The present invention relates to molecular quantification of nucleic acid sequences, and provides systems and methods for improvements in real-time data collection and in real-time signal analysis. In some embodiments, said improvements are applied to limiting dilution methods for nucleic acid quantification, hitherto analyzed only by end-point methods.

As used herein, "sequence" means the order, number, and identity of nucleotide bases that compose a DNA or RNA molecule, or the order, number, and identity of nucleotide bases that compose a subset of said molecule. As used herein, "quantification" means a determination of the number of specified sequences in a given sample. In some embodiments, said sample may be in liquid form and the units of quantification may be expressed in number of sequences per volume of liquid. The abbreviation "log" is used for logarithmic transformation (e.g., "log(signal)").

As used herein, "aliquoting" means the dispensing of an initial volume to multiple equal smaller volumes, and "aliquots" refers to said multiple equal smaller volumes. As used herein, "reaction core mixture" means the components of a biochemical amplification mixture, typically containing but not limited to: one or more enzymes; ionic components that establish a desired ionic strength and ionic composition; and a buffer for control of reaction pH. A reaction core mixture may be assembled at an initial concentration that is greater than the final reaction concentration, so that said reaction core mixture may be brought to final reaction concentration by addition of a liquid volume, said liquid volume possibly being a sample that is to be assayed. As used herein, "reaction mixture" comprises a reaction core mixture at final reaction concentration, where said reaction mixture may contain amplification templates. As used herein, "replicate reactions" means aliquoting a reaction mixture to nominally identical reaction chambers; in contrast, "replicate assays" would refer to aliquots of a reaction core mixture in nominally identical reaction chambers, wherein sample volumes are individually added to said aliquots.

Substances of interest are frequently present in small amounts in a sample collected for analysis. A biochemical method for estimation of the amount of a substance is the specific amplification of said substance, or the specific amplification of a marker that is attached to said substance. A signal proportional to the amount of amplification is measured during or after the amplification process. If the amount and rate of amplification are known, said signal can be used to estimate the amount of starting material. Estimation of an initial amount given the nature and degree of amplification can be illustrated by analogy to a bank account. If the present amount of money in a bank account is known, as well as the continuously-compounded interest rate and the time of accrual, then the initial amount can be calculated. Both the interest rate and time on deposit must be known to make the calculation.

The accuracy of methods that calculate initial quantities from amplified quantities is dependent on knowledge of the nature of the amplification; for calculation of initial quantities, a mathematical model of the amplification process is preferred. For biochemical amplification, mathematical models are derived from the biochemical reaction mechanism. Two amplification methods that are useful in molecular diagnostics are the polymerase chain reaction (PCR) and two-primer ramified rolling circle amplification (RAM). Models of the PCR and RAM reactions predict that each reaction ideally should exhibit exponential amplification. Other amplification methods may share a model but achieve amplification by different biochemical methods; for example, helicase-dependent amplification (HDA) and recombinase polymerase amplification (RPA) implement a PCR-like mechanism without thermal cycling. Still other amplification methods have been described with mechanistic diagrams, but have not yet been reduced to formal mathematical models (e.g., loop-mediated isothermal amplification; LAMP).

Measurement of nucleic acids by amplification was initially an endpoint procedure that was interpreted as revealing the presence or absence of a target sequence, and possibly a tentative assessment of target quantity. Estimation of target quantity was greatly improved by the advent of instruments that repeatedly detect and record a signal that is proportional to the amount of an amplification product. Said instruments are called real-time amplification detection systems; said systems provide a signal that is proportional to the progress of the amplification reaction. Amplification reactions that are performed in real-time amplification detection systems are called real-time reactions.

FIGS. 1A-D provide examples of plotted data from real-time reactions generated from PCR reactions and RAM reactions. In real-time RAM or PCR reactions the early amplification products are not directly observed, because the signal due to those early amplification products does not rise above a basal, or baseline, level (see, e.g., FIG. 1A and FIG. 1B); the pre-amplification signal is attributable to instrument noise or other factors. The initial basal signal is followed by a transition period where the observed signal is the sum of basal noise and amplification signal; this transition period occurs as amplification products accumulate to a point such that the signal due to those products becomes greater than the basal noise level. Exponential change of signal with respect to time, ideally, follows the transition out of the basal level. Following a period of exponential change, the amplification rate slows as expected of an exponential reaction in a limited volume (said amplification rate change is due at least in part to reactant limitation, changed reaction chemistry, or product inhibition). In both RAM (FIG. 1B) and PCR (FIG. 1A) the exponential growth rate decreases to a plateau, after which signal does not change significantly with respect to time.

RAM and PCR produce similar fluorescence-signal curves in real-time reactions, as shown in FIG. 1. However, there are substantive differences between the isothermal RAM reaction and the thermocycling inherent to PCR. The thermal cycle is a necessary component of the PCR process. Real-time measurements of PCR reaction progress provide a single observation per thermal cycle or provide a single statistical summary per thermal cycle. PCR product yield at fractional cycles can be estimated, but is not, at the present state of the art, measured or analyzed. A common analysis method for PCR is to compute a fractional cycle at a signal threshold; the fractional cycle is reported as a cycle threshold (Ct) or quantification cycle (Cq).

There are few PCR cycles in which the amplification is in exponential phase. Identifying cycles that exhibit characteristics of exponential signal change is important because it is assumed that it is only in the exponential phase that the fractional cycle reflects the input template level. Ideally, the fractional cycle at which the Ct/Cq is estimated should be in the exponential change region of the amplification. However, due to the paucity of exponential phase PCR cycles, distinguishing those cycles is not a simple or straightforward process.

The RAM reaction can be analyzed as a continuous time-dependent process rather than a discrete cycle-dependent process; the time to reach a threshold fluorescence is designated the response time (Rt) corresponding to the cycle threshold of real-time PCR. The natural unit of isothermal amplification is product yield per time unit, just as product yield per thermal cycle is the natural unit of PCR. Unlike cycle number, time is continuous and can be infinitely subdivided; therefore, product yield measurement frequency of isothermal amplification is limited only by instrument capacity.

The utility of finding the exponential phase PCR cycles has motivated a series of publications that continue on after more than two decades, describing a variety of methods for PCR analysis. These methods can generally be divided into two groups: first, parametric methods that seek to fit mathematical models by parameter fitting to the data; and second, non-parametric methods that extract statistical measures directly from the data. Non-parametric approaches to exponential phase signal determination include mathematical operations on the signal such as computing the fractional cycle at which the second derivative of the signal vs. cycle data is at a maximum. Parametric, or model-fitting, methods are a more computationally intensive process. Some reported procedures fit a mathematical object having similarity to the whole reaction signal (baseline, amplification, signal plateau). Others have extensively refined model-fitting techniques; their computer applications find parameters of the fitted model, and analyze points or regions of the fitted object.

Identification of the PCR exponential amplification phase has at least two motivations: determination of Ct/Cq, and determination of the PCR reaction efficiency. Accurate comparison of multiple PCR reactions requires an estimate of each reaction's efficiency. Ideally, each PCR cycle should yield twice as much product as the previous cycle. However, various factors including sub-optimum primers, amplification inhibitors in the sample, or sub-optimum reaction chemistry can result in less than ideal exponential growth; therefore, comparison of two PCR reactions with different efficiencies can lead to inaccurate estimates of initial amounts.

A substantial effort has been devoted to defining PCR efficiency; for example, the online bibliography at www.gene-quantification.de/efficiency.html lists more than 50 publications devoted to various aspects of defining and applying measures of PCR efficiency. These and other publications provide examples of definition and analysis of regions of PCR data. In parametric modeling the model that is fitted to the data is not, however, the exponential growth ideally observed in PCR; instead, the fitted models are used to find the exponential region.

An essential input to some model-based methods of finding the exponential region in current PCR methods is finding the signal baseline, defined as the early signals that do not change much over time. Various methods for finding a PCR baseline have been described.

Practical applications of specific nucleic acid sequence detection require comparison among multiple samples; said samples might include, for example, positive controls for amplification and/or a set of standard concentrations of known targets. Absolute quantification, expressed in numerical units of target molecules, has not yet been accomplished via real-time amplification monitoring, as evidenced by the adoption of digital PCR, which abandons real-time methods in favor of endpoint detection and statistical analysis. However, accurate quantification via PCR has encountered both practical and theoretical limits. Practically, the difficulty of per-reaction efficiency measurement has limited PCR quantification, and Poisson variance at limiting dilutions has made quantification at less than 5 to 10 template copies per reaction theoretically challenging. Some researchers have turned Poisson limiting dilution effects from a problem into an advantage by abandoning any use of real-time signal analysis, instead using endpoint detection and statistical inference of template copy number after sample dilution.

Poisson statistics in this context describes the distribution of small numbers of events. For example, if ten marbles are tossed randomly into ten cups, one cup may get two marbles and another cup may get no marbles. If the number of marbles tossed is less than the number of cups, some cups are guaranteed to be empty; and the ratio of empty to non-empty cups could be used to estimate the original number of marbles, given the number of cups. The Poisson distribution is a statistical tool that could be used for predicting how many cups get some number of marbles. After the tossing, the Poisson distribution could be used to predict, from a count of marbles from a sample of cups, how many marbles were tossed. The Poisson distribution is an appropriate model for the partitioning by dilution of samples for molecular diagnostics.

The present invention provides, in various embodiments, improvements in molecular measurement methods using amplification. The description herein is illustrated with data from an amplification using RAM (FIG. 1B), but the invention is not limited to that reaction mechanism. For example, in alternative embodiments, other isothermal systems may be used for high-frequency sampling. The methods described herein have utility with any amplification method where sufficient samples that fit a mathematically defined region can be obtained. Examples of suitable amplification methods include, but are not limited to, RAM, primer generation-rolling circle amplification, amplification via recombination proteins (RPA), loop-mediated amplification on circle-substrate, real-time NASBA (Nucleic Acid Sequence Based Amplification) with beacons, and helicase-mediated isothermal PCR (HDA).

The PCR is not sampled uniformly in the sense described here because a single data point per PCR cycle is observed (or computed). Although the sampling is regular, the reaction is not sampled uniformly in the exponential signal change region of interest. In alternative embodiments, the methods provided herein could be applied to uniform sampling of thermocycling PCR with appropriate product accumulation or product accumulation marker detection systems; however, correction for differential rate of product accumulation vs. time in non-uniform reaction environments (e.g., thermal denaturation cycles, thermal ramping) would preferably be made. A reaction temperature datum would preferably be recorded for each time point and product measurement.

Previous methods used the intersection of a line generated by an exponential model fit to the amplification region of a RAM reaction and the baseline of that RAM reaction to define a response time. Such computations require a baseline definition (as noted above, not a trivial operation) and, as described, do not compute or consider efficiency.

Figure 2:
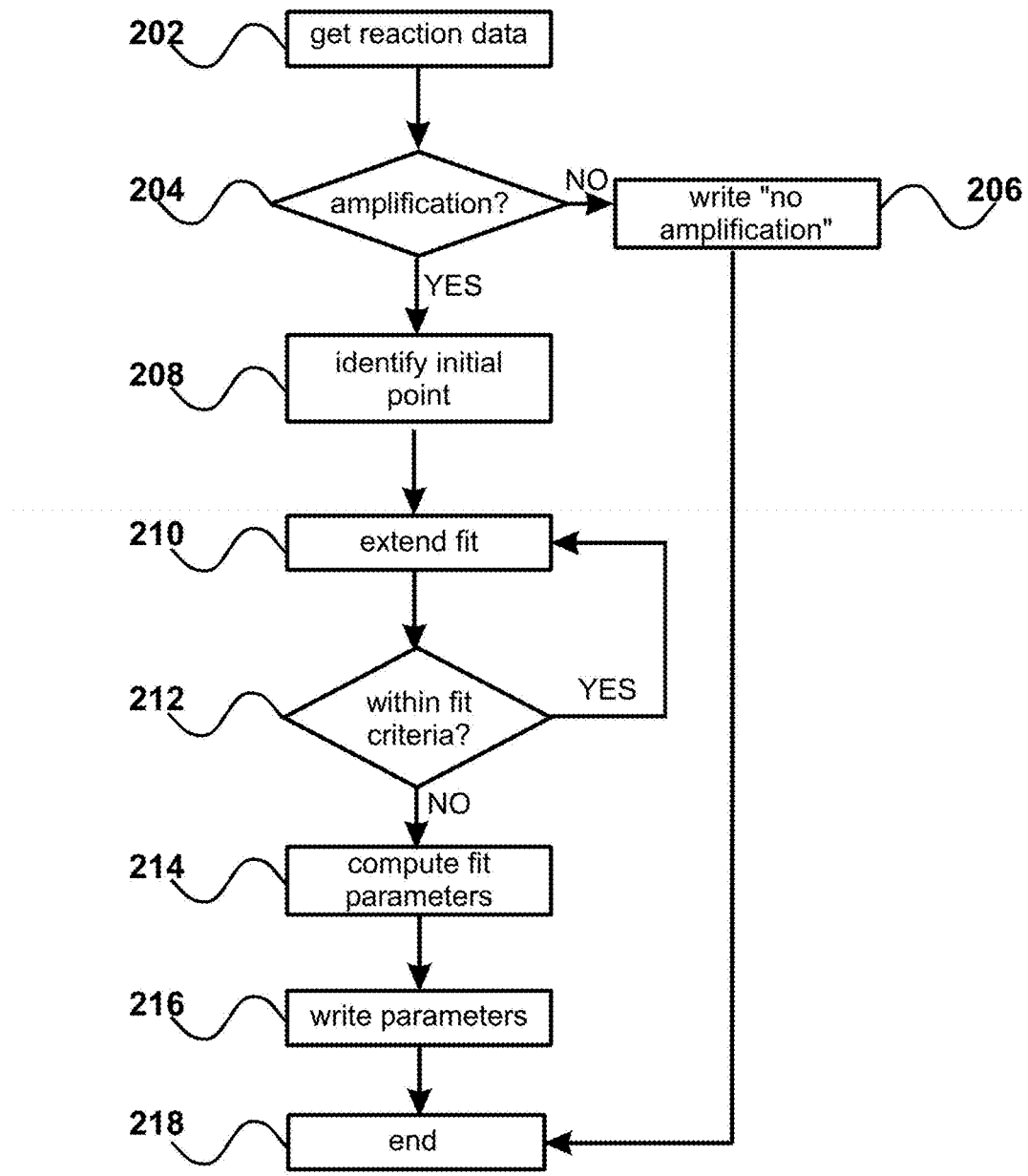
FIG. 2 shows an exemplary flowchart for a computer-implemented assessment of a single amplification reaction, according to some embodiments.

FIG. 2 shows an exemplary flowchart for computer-implemented assessment of a single amplification reaction, according to some embodiments. At step 202, amplification data are read into a table; then at step 204 a decision is made as to whether a significant amplification has occurred (see, e.g., FIG. 3). If no amplification has occurred, this result is noted at step 206 and the evaluation is ended at step 218. If an amplification has occurred then at step 208 an initial point for evaluation is chosen. From the initial point, additional points are added at step 210 and evaluated at step 212 until a next point causes the collection of points to fail predetermined evaluation criteria. The chosen collection of points is evaluated to compute fit parameters at step 214 and statistical measures of the chosen collection of points are recorded (e.g., written to a table) at step 216, completing the evaluation of the current reaction at step 218.

Figure 3:
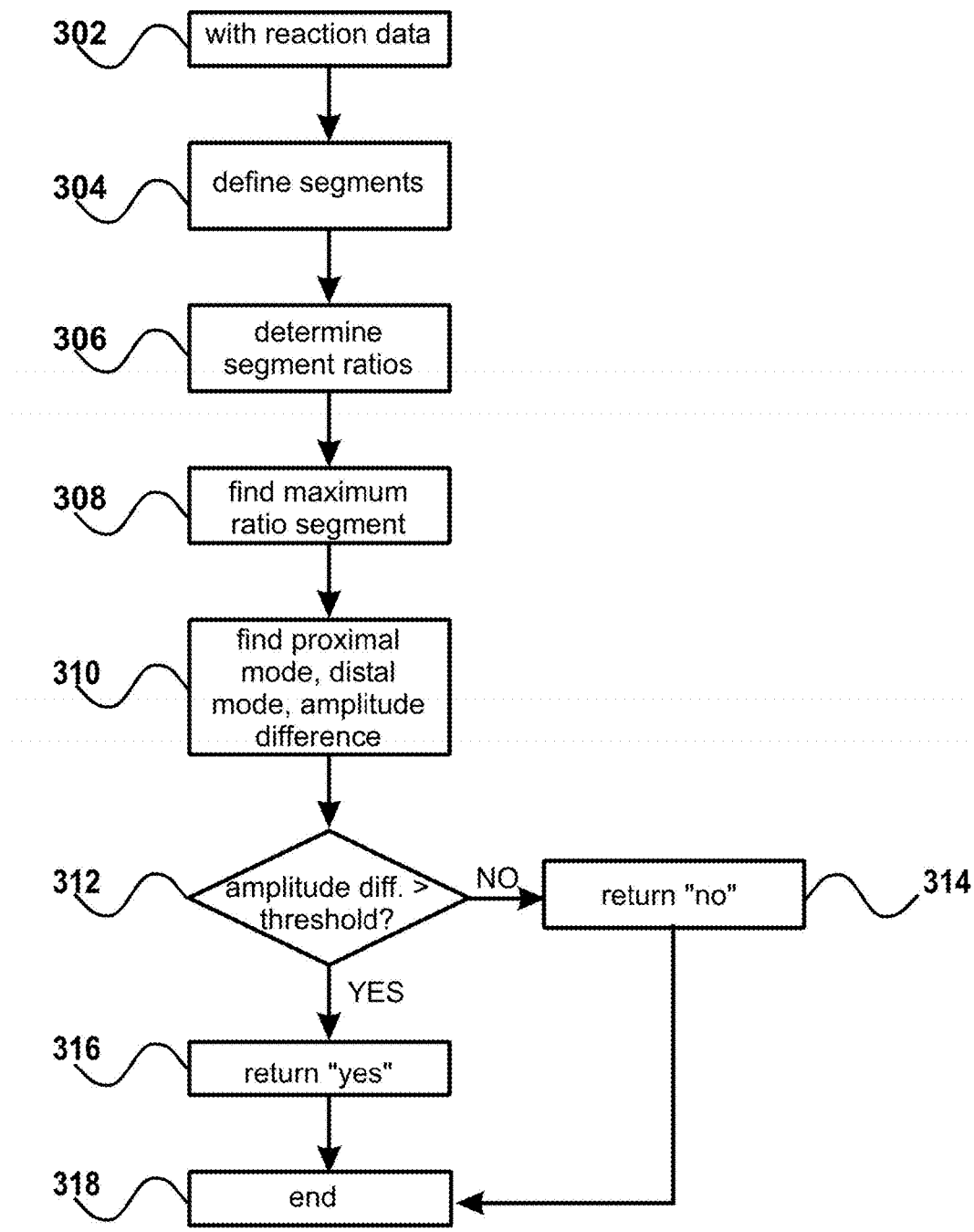
FIG. 3 shows an exemplary flowchart for a computer-implemented assessment of whether amplification has occurred, according to some embodiments.

FIG. 3 shows an exemplary flowchart for a computer-implemented assessment of whether amplification has occurred (step 204), according to some embodiments. In some embodiments, the input data to the algorithm at step 302 is a set of (time, signal) data, obtained, for example, at FIG. 2 step 202. Said data is evenly sub-divided into multiple segments at step 304. Segments are divided into proximal and distal halves, segment ratios are computed at step 306, and a maximum sub-segment ratio is determined at step 308. At step 310, the modes of the signal data are determined, and the reaction amplitude is defined as the difference between the baseline mode and the plateau mode. The amplitude difference is evaluated at step 312. If the amplitude is greater than a preset threshold value ("YES" at step 312) then amplification is deemed to have occurred at step 316, the analysis of FIG. 3 ends at step 318, and the analysis of FIG. 2 proceeds to step 208; otherwise ("NO" at step 312) no amplification is deemed to have occurred at step 314, the analysis of FIG. 3 ends at step 318, and the analysis of FIG. 2 proceeds to step 206.

Based on the values for the parameters of the model (e.g., as recorded at step 216), the present invention further comprises determining a value representative of an initial condition of the sample. In some embodiments, the value is a value representative of an amount of a nucleic acid sequence in the sample. For example, the system may display to the user an estimate of copy number (e.g., for Downs syndrome fetal diagnostics: "2 copies of Chromosome 21" for the normal euploid complement). In another embodiment, for process optimization, the system may display to the user a message such as: "Condition A results in an 0.1× increase in slope compared to condition B." The systems and methods of the present invention are adaptable, multi-purpose tools, and the preceding examples represent only two out of many possible output displays from two exemplary uses.

Figure 1B:
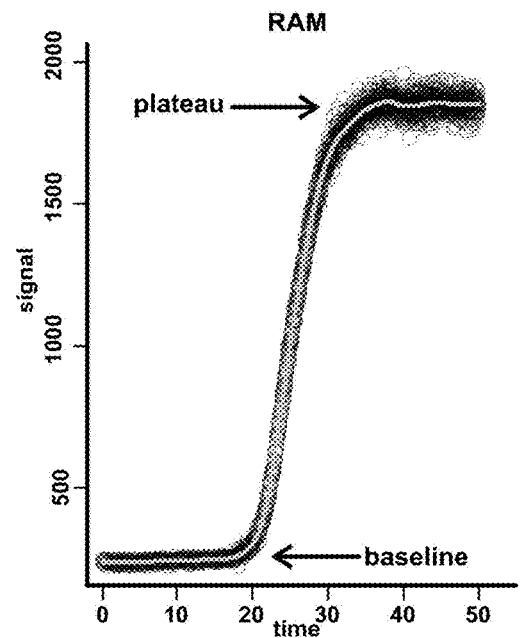
Figure 1C:
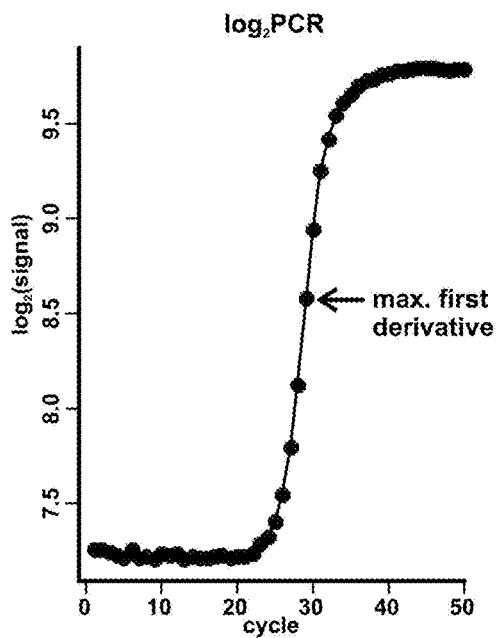
Figure 1D:
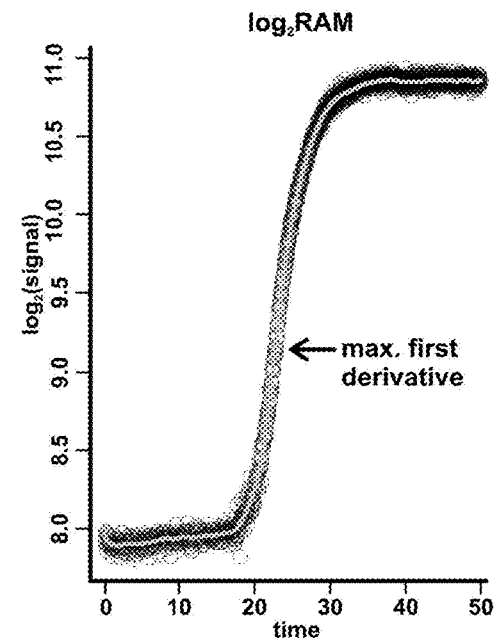
Figure 4A:
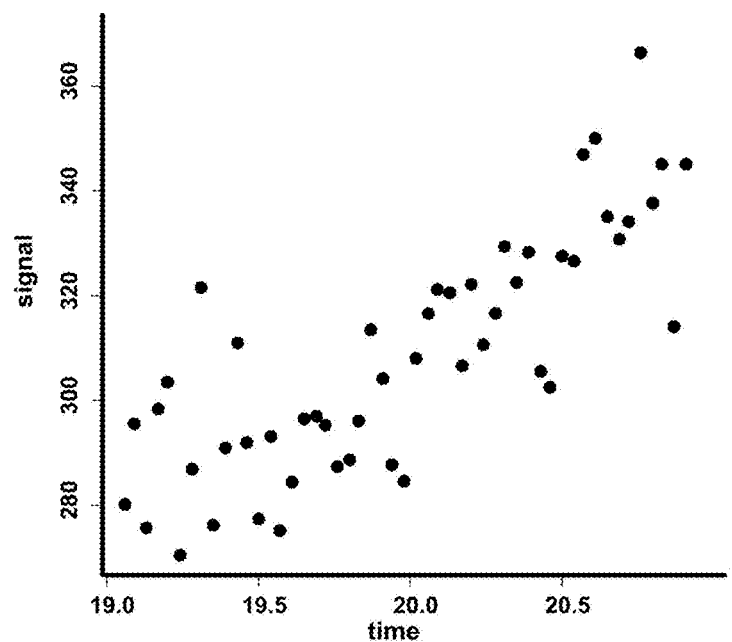
FIG. 4A shows a detailed view of the data of FIG. 1B, showing local data variance among individual data points at the time in the amplification reaction when the amplification signal begins to exceed the background signal level.

FIGS. 1B and 1D show data points collected at high frequency from a typical isothermal amplification reaction (a RAM reaction). These data were analyzed by the steps shown in the flowcharts of FIGS. 2 and 3, as described below. The data density provided by the methods described here necessitated statistical methods to distinguish local data variance from larger trends. FIG. 4A illustrates the variance in the (time, signal) data points in the region where the amplification signal initially rises above the baseline.

Figure 4B:
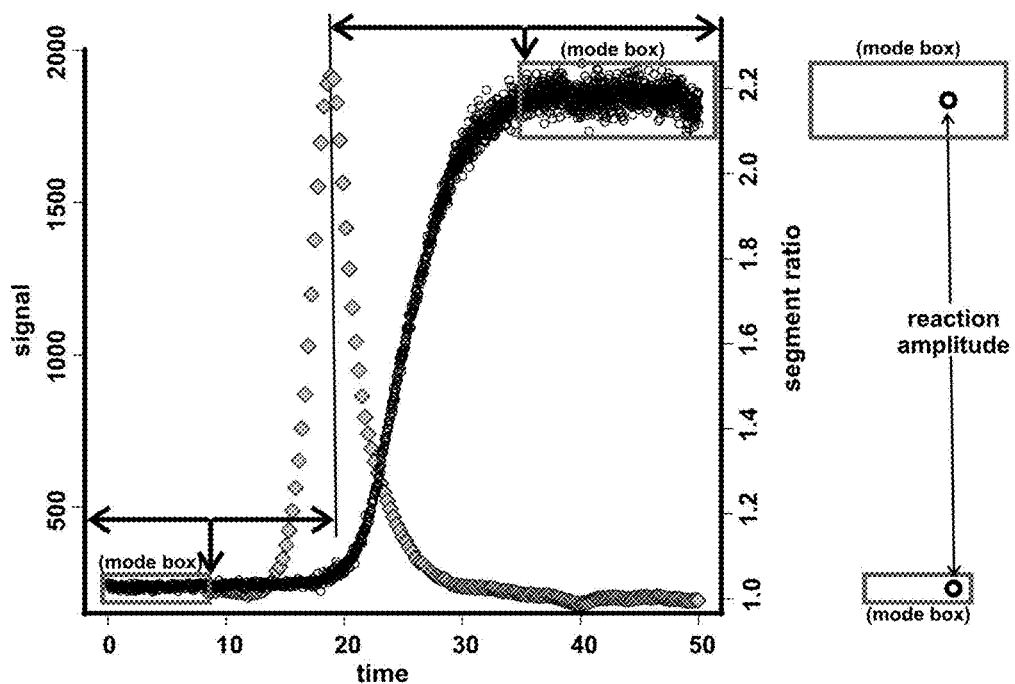
FIG. 4B illustrates exemplary aspects of the method that is used to determine whether an amplification reaction has occurred. Open circles represent the data points of FIG. 1B; grey-filled diamonds are the segment-ratios. A vertical line indicates the maximum segment-ratio. The position of said maximum segment ratio defines larger segments (double-headed arrows):a proximal segment containing the baseline, and a distal segment containing the plateau. Said larger segments are divided into proximal and distal halves, with sub-segments containing the baseline signal region and the plateau signal region marked by grey boxes labeled 'mode box' where modal values are determined from the data. The right side of FIG. 4B shows a schematic representation of the mode-boxes with a graphic circle representing the modes, and the reaction amplitude defined as the difference between the modes.

A set of (time, signal) data was accessed (step 202), and a decision as to whether an amplification occurred (step 204) was made as follows, according to the process shown in FIG. 3. Reaction data input at step 302 was subdivided into multiple segments (step 304); the segment size may vary depending on the number of data points and the data variance. Each segment was equally divided into an earlier set of signal data points and a later set of signal data points. A segment ratio was computed for each segment by dividing the sum of the distal signal data by the sum of the proximal signal data (step 306). The set of segment ratios are indicated graphically by diamonds in FIG. 4B. The maximum segment ratio was determined (step 308), and used to define two larger data segments: a baseline segment extending from the start of data to the maximum segment ratio, and a plateau segment from the maximum segment ratio to the last data point (said larger segments are illustrated in FIG. 4B). Said larger segments were subdivided by halves into a proximal baseline segment and a distal plateau segment, shown by graphic boxes in FIG. 4B. The statistical mode of each said sub-segment was determined, and the reaction's amplitude was defined as the difference between the mode of the proximal baseline segment and the mode of the distal plateau segment (step 310). When the amplitude was greater than a predefined value ("YES" at step 312), the reaction was scored as having an amplification signal (step 316); otherwise ("NO" at step 312) the reaction was scored as no amplification (step 314).

In alternative embodiments, other processes for computer-implemented assessment of whether amplification has occurred may be used for the conditional of step 204, which may vary in complexity and computation time per data set; the method is not limited to the process described and shown in FIG. 3 and FIG. 4B. For example, in other embodiments, amplification/no amplification could be detected by analysis of spline fit parameters, or by parametric fitting of a sigmoid model (as is done in some PCR analysis methods).

Figure 6A:
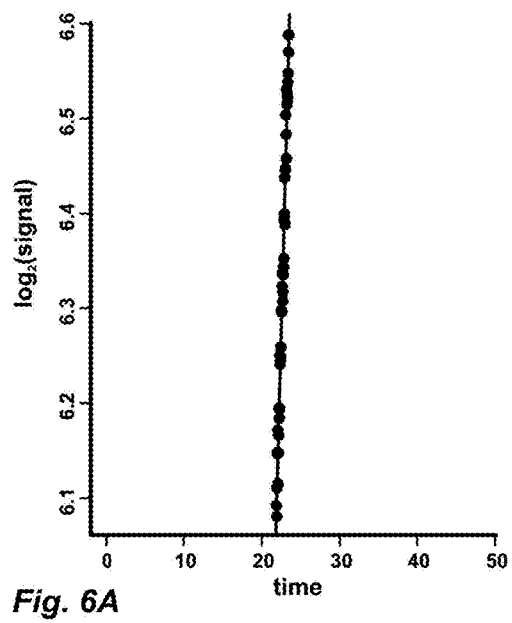
FIGS. 6A-D illustrate an exemplary application of the described methods to the amplification data shown in FIG. 1D and in replicate reactions to said amplification data.

Identification of an initial point of interest (step 208) was accomplished by fitting a smoothing spline to the data (the smoothing spline is represented by a gray line in FIG. 1D). A first derivative maximum was obtained from the fitted spline, completing step 208. In alternative embodiments, other methods for selecting an initial point may be used (e.g., a segment-wise evaluation could be used, wherein the whole data set is segmented, $R^2$ correlation coefficients are determined for each segment, and an optimum segment is chosen; or a second derivative from a spline fit could be used). A fixed region around said first derivative maximum was chosen, then a linear model was fitted to said region around said first derivative maximum. A correlation coefficient ($R^2$) was computed for the current region. Then the region was extended for a defined step size (step 210), and a second correlation coefficient ($R^2$) was computed for the extended region. When the difference between the first and second correlation coefficients did not exceed a set maximum ("YES" at step 212), the extended region was redefined as the current region. Otherwise ("NO" at step 212), the current region was taken as the preferred data subset for the current reaction, and statistical measures describing said subset (step 214) were written (step 216) to a data table. In this example, said measures of said subset included: a least-squares linear regression fit to the [log(signal), time] data; the slope and Y-intercept; the correlation coefficient ($R^2$); the variance; and the time points defining the start and end of said subset. In alternative embodiments, other statistical measures or other combinations thereof may be used. FIG. 6A illustrates the data points of a subset extracted as described from the data of FIG. 1D, with a fitted line generated by the slope and Y-intercept derived from a linear regression model fitted to the log-linear data as described.

The Y-intercept is the point at which said fitted line crosses the Y-axis. Said Y-intercept is a hypothetical fluorescence signal at time 0 (zero); a greater initial template at time 0 will have a greater Y-intercept, if slopes are equal. The Y-axis is demarcated in units of signal, not copy number, so Y-axis intercepts may be below a nominal 0 (zero) level. Slope, in isothermal reactions, is product increase over time; the PCR equivalent is efficiency, product increase per thermal cycle. A per-reaction efficiency measure is a long-sought but not-yet achieved goal for PCR; high-frequency data sampling and analysis as presented here accomplish that goal for isothermal amplifications.

Figure 5A:
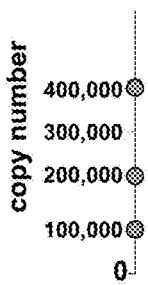
FIGS. 5A-H show a conceptual explanation and rationale for evaluating results from a set of replicate reactions.

The per-reaction slope and Y-intercept scores would, a priori, both be significant in the interpretation of isothermal reactions. The slope and intercept significance is illustrated conceptually in FIGS. 5A-H, before further presentation of experimental data. Consider three sample solutions containing different concentrations of a DNA sequence, and suppose those concentrations are sufficient for DNA concentration measurement (e.g., by measuring fluorescence emission after addition of a suitable dye). These measurements can be represented as points on a vertical axis, as shown in FIG. 5A, where the sample amounts are represented as doublings in the ratio 1:2:4.

Figure 5B:
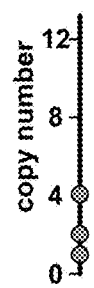
Figure 5C:
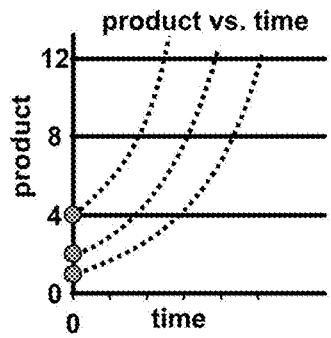
Figure 5D:
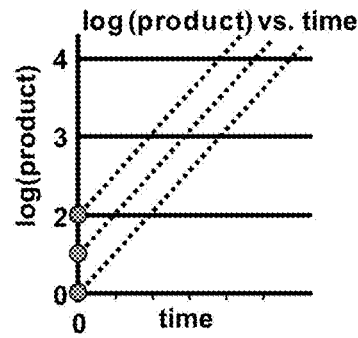

Suppose samples from said three solutions each to be ideally diluted, said dilution maintaining the copy number ratio, such that direct measurement of DNA sequence is no longer possible, and with a maximum dilution such that the lowest DNA copy number is as low as one (1) copy per sample. FIG. 5B represents the (now not directly measurable) DNA concentrations of the diluted samples on a vertical axis. Suppose the diluted samples are amplified by an ideal exponential amplification system, so that FIG. 5C represents the amplification process as product accumulation over time. FIG. 5D depicts a logarithmic transformation of the product yield plotted against time, resulting in a linear relation of log(product) vs. time.

Figure 5E:
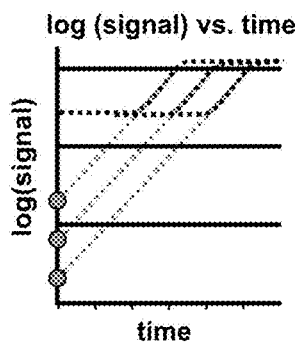
Figure 5F:
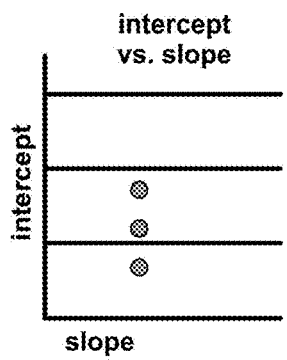

FIG. 5E illustrates what is seen in real-time monitoring of exponential amplification by overlaying the idealized amplification time course with a representation of a real-time signal trace (e.g., FIG. 1D). In this idealized system, the slopes of the amplification time-course are all equal; in isothermal amplifications this would indicate equal rates of product synthesis over time, and in PCR equal slopes would indicate identical reaction efficiencies. Therefore, FIG. 5F shows that if the time-zero intercept in FIG. 5E is plotted on a vertical axis, and the (equal) slopes corresponding to those intercepts are plotted on a horizontal axis, the result is a vertically aligned set of points that is proportional to the logarithms of the initial substrate amounts that were amplified. The vertical data of FIG. 5F are an idealized experimental determination of the ratios of the starting material of FIG. 5B.

Figure 5G:
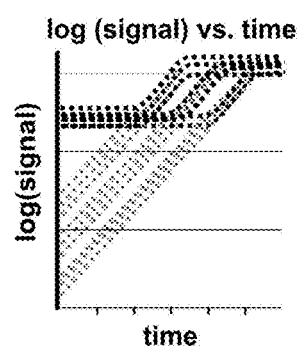
Figure 5H:
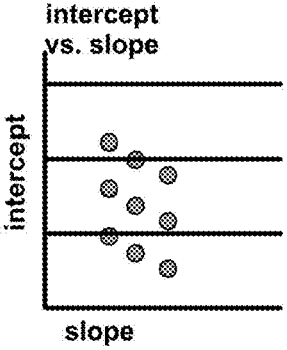

In actual amplification systems, experimental noise introduces statistical error into estimates of slopes; and replication provides a means of estimation of the magnitude of said statistical error. FIG. 5G depicts replicate amplification reactions, wherein each said replicate reaction provides a slope and an intercept. FIG. 5G shows that slope variation results in intercept variation, wherein greater slopes result in lower intercepts. Therefore, when slope is plotted on an increasing scale, the corresponding intercepts decrease in magnitude as shown in FIG. 5H.

Figure 6B:
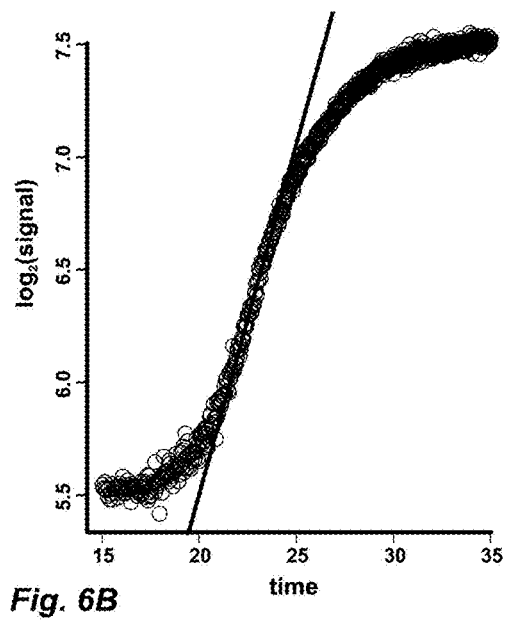
Figure 6C:
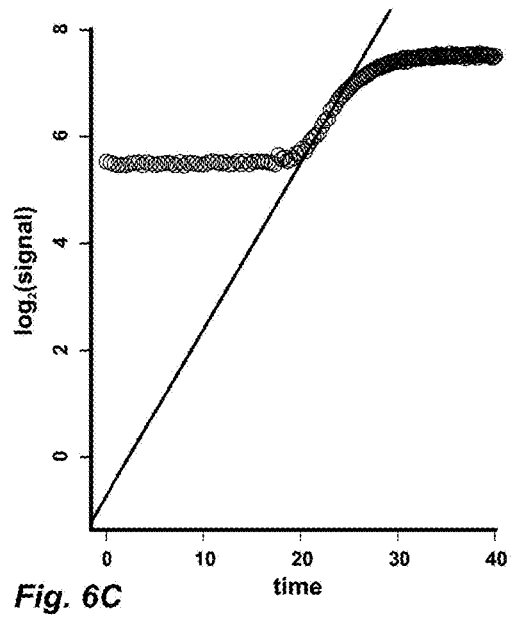
Figure 6D:
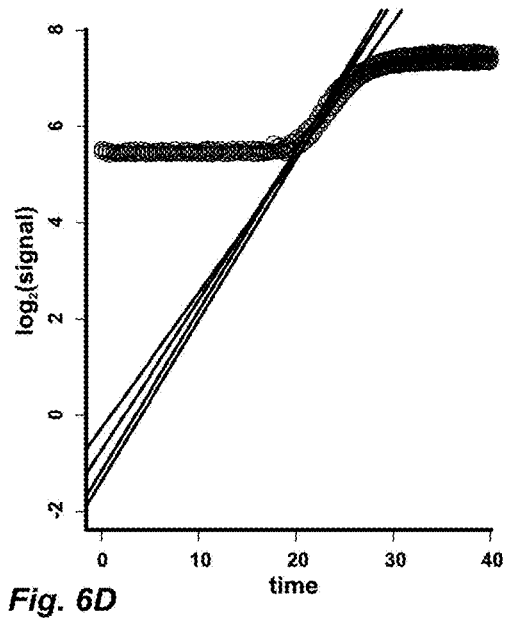

FIGS. 6A-D show experimental data illustrating some aspects of the theoretical treatment of FIGS. 5A-H. FIG. 6A shows data points identified by the procedure shown in FIG. 2, from the data of FIG. 1D, as well as a line defined by a linear model that was fit to those data. FIG. 6B illustrates said fitted line over a larger subset of the FIG. 1D data from baseline to plateau. FIG. 6C shows all the baseline data on an extended vertical axis to illustrate the Y-intercept of the fitted line, and FIG. 6D shows data from three additional replicate reactions, illustrating with experimental data the conceptualization of FIG. 5G.

The experimental data from which the graphics of FIGS. 1A-D and 6A-D are derived included two different dilutions that were made from a single source stock of single-stranded DNA circles. The amount of dilution was calculated to be such that some aliquots of each dilution would be predicted from Poisson statistics to include some aliquots without any template molecules. An aliquot of each dilution was added to a reaction core mixture to create two reaction mixtures, and said reaction mixtures were aliquoted to multiple reaction chambers. 45 replicate RAM reactions were performed in a real-time instrument for each reaction mixture; said instrument was programmed to obtain real-time data at the shortest possible time-intervals. Said data was processed by a set of scripts implemented in the "R" system for statistics such that each reaction was evaluated according to the processes shown in the flowcharts of FIGS. 2 and 3. A table of statistical measures was constructed for reactions in which an amplification was detected, and the number of reactions in which no amplification was detected was likewise recorded.

Figure 7A:
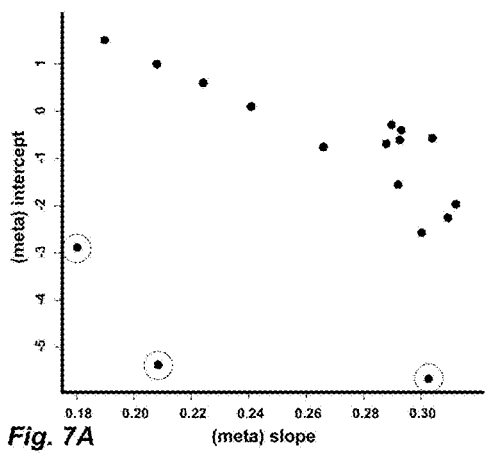
FIGS. 7A-D show data from two sets of replicate reactions initiated from two different RAM template dilutions. For both sets of results, an initial panel and a post-data-quality-control panel is shown.
Figure 7B:
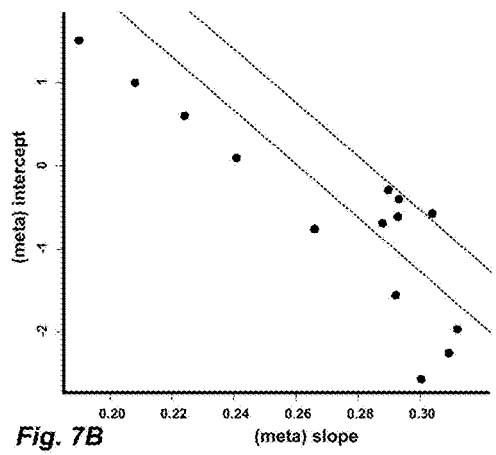

FIGS. 7A and 7B show plots of data from the more dilute of the two dilutions. The 17 data points of FIG. 7A show the slope and intercept of each positive reaction. The 62% failure rate implies a Poisson estimated mean of 0.47 template molecules per reaction. Initial statistical evaluation showed that three of the 17 data points of FIG. 7A had lower $R^2$ correlation coefficients and later response times; those data were eliminated from consideration and the remaining points appear in FIG. 7B. These points fall along a negative slope as depicted in FIG. 5H. Applying Poisson statistics further indicates that for 45 samples at a Poisson mean of 0.47, about 13 samples at one template per sample are expected, about three samples at two templates per sample are expected, and there is about a 50% chance of seeing one sample with three templates. Dashed lines plotted in FIG. 7B show that the multiple diagonals anticipated from FIG. 5H separate consistent groups of data points.

Figure 7C:
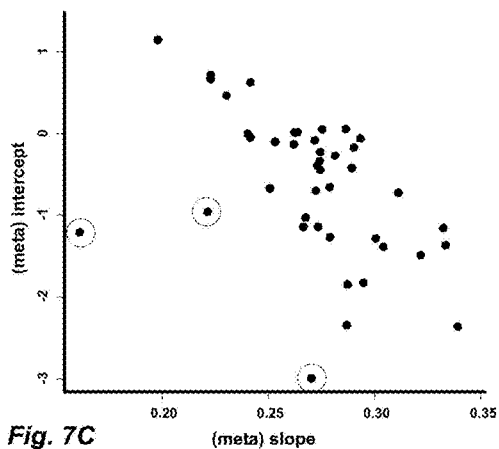
Figure 7D:
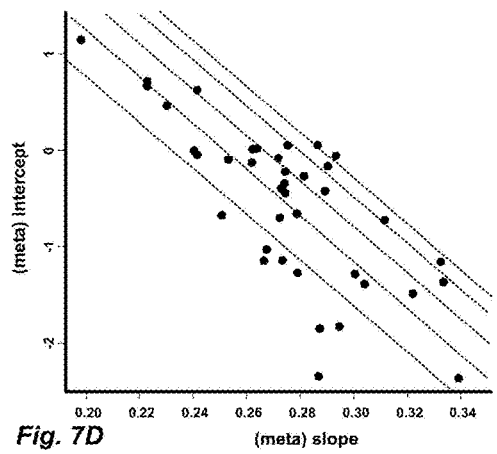

The second dilution prepared as described above was designed to have a four-fold greater number of template molecules per sample. FIGS. 7C and 7D show plots similar to FIGS. 7A and 7B, with FIG. 7C showing all data points from the less dilute sample, and FIG. 7D showing data points excluded as outliers. Three failures out of 45 replicate reactions implies a Poisson mean of ~2.7 template molecules per reaction tube. Arranging diagonal separator lines as for FIG. 7D reveals a distribution of data points consistent with Poisson expectations.

The results shown in FIGS. 7A-D demonstrate that the methods of the present invention can facilitate the identification of amplification reactions that contain one and only one template molecule. The present invention's use of slope, intercept plots for estimating small copy numbers is in the general field that is now served by digital PCR. As currently practiced, only product/no-product ratios obtained from replicate reactions are used in statistical analysis of digital PCR assays, and real-time data is not collected. The results shown here illustrate the utility of collecting real-time data from isothermal reactions on samples made by appropriate dilutions, or of assays on undiluted samples of appropriate concentrations. The utility of the identification of amplification reactions that contain a single template molecule includes the potential greater efficiency of target concentration estimation when a count of single molecule reactions is combined with a proportion of reactions that fail to amplify and are interpreted as containing zero template molecules. Further efficiency of target concentration estimation may result if the number of two-template molecule amplifications can be estimated, and so on for greater template molecule numbers.

In alternative embodiments, the methods of the present invention may be applied to digital PCR. Digital PCR requires some zeros, and thus requires a large number of wells when the average copy number per reaction is high. A system based on the methods disclosed herein, optionally with some added wells for standards, can advantageously provide accurate concentration estimates without any zero wells.

The methods described herein may also be used for assay optimization. The present invention recognizes that distinguishing one-template amplifications from 2-, 3-, or more-template amplifications can be more reliably done if the target-number groupings (as shown in FIGS. 7B and 7D) are well-separated. In addition, experimental manipulation of reaction conditions may allow a greater separation of the target-number groups that are shown separated by dashed lines in FIGS. 7B and 7D. Further, the methods of the present invention provide improved accuracy in reaction rate determination.

In cases where no mathematical model for reaction rate has been defined but densely sampled data can be obtained, data can be sampled as described above. In some embodiments, the present invention contemplates finding inflection points using derivatives of such data, regions where the amplification rate changes; said points may, for example, be correlated with experimentally defined factors and used for process optimization.

As new isothermal amplification methods continue to be described there is an ongoing need to elucidate reaction mechanisms and to optimize reaction conditions. Process optimization using statistical design of experiments (DOE) will also benefit from the methods disclosed here. In DOE, multiple experimental factors (such as reagent concentrations, or reaction conditions such as temperature) are systematically changed and the effects of those changes are measured; a strength of DOE is the detection of interacting factors where a combination of factors has a greater effect than the sum of the effects of the separate factors. Analysis of such experiments is facilitated by variety and detail of descriptive data; therefore, DOE methods applied to biochemical amplification reactions will benefit greatly from the methods disclosed here due to the detailed recording of the reaction process.

Some amplification methods may not produce data subsets to which linear models can be fitted, either to raw data or to data after the logarithmic transformations used for RAM or PCR. Where no linear model can be fitted the data density yielded by the present methods can still prove advantageous by allowing the fitting of well-defined non-linear models, and those models may be useful in elucidating reaction mechanisms. In cases where no well-defined model can be fit, the data density revealed by the methods disclosed here may still be used to advantage, for example in the empirical piece-wise or segment-wise fitting of polynomial splines.

The applications of the methods described herein represent only a few examples of the utility of high-frequency biochemical amplification data collection and analysis. Automated detection of noise signals and other quality-control applications are contemplated in further embodiments. The methods of the invention disclosed herein provide improved estimates of significant parameters, applicable in many areas of analysis.

While there have been shown and described fundamental novel features of the invention as applied to the preferred and exemplary embodiments thereof, it will be understood that omissions and substitutions and changes in the form and details of the disclosed invention may be made by those skilled in the art without departing from the spirit of the invention. Moreover, as is readily apparent, numerous modifications and changes may readily occur to those skilled in the art. Hence, it is not desired to limit the invention to the exact construction and operation shown and described and, accordingly, all suitable modification equivalents may be resorted to falling within the scope of the invention as claimed. It is the intention, therefore, to be limited only as indicated by the scope of the claims appended hereto.

Example 1

This example describes amplification of a single-stranded, nucleic acid target, according to some embodiments of the invention. A C-probe with gene-specific termini that are specific for the wild-type locus of the human Factor V gene was 5' phosphorylated, then circularized and amplified as described below to provide an amplification substrate for 2-primer ramified rolling circle (RAM) amplification and analysis.

A ligation reaction was made by combining synthetic ligation target TgtFctVWT+(5'pAGAGACATCGC-CTCTGGGCTAATAGGACTACTTCTAATCTGTAA GAGCAGATCCCTG) (SEQ ID NO: 1) to 9 µM; C-probe Cpr8FVWt1 (5'GCCTGTCCAGGGATCTGCTCTTA-CAATACGAGAACACCCGAT TGAGAGAGTTTG-GAAGTGTAGGCGTGAAGTCCATAACACATACCTGT-ATTCCTC) (SEQ ID NO: 2) to 6 µM, Taq DNA Ligase buffer (New England Biolabs, Ipswich, Mass.) to 1×, Taq DNA ligase (New England Biolabs, Ipswich, Mass.) to 0.8 units/µl, and water to 100 µl volume. The reaction mixture was incubated at 95° C., 30 sec for initial denaturation then cycled five times through the following regimen: 30° C., 1 min for hybridization; 65° C., 30 sec for ligation, then 95° C., 10 sec for denaturation.

An estimate of circular, single-stranded DNA template concentration was made, bearing in mind possible sources of error: random error with mean zero effect and error based on 100% optima assumption where real percentages less than 100% result in lower template concentration. Examples of the former error types include the algorithmic assignment of an extinction coefficient to the C-probe, error in spectrophotometric measurement, and liquid handling error. Idealized 100% assumptions include: the assumption that 100% of the C-probes are full length and capable of ligation after hybridization on the target; that 100% of the C-probes are phosphorylated after exposure to kinase enzyme; and that 100% of the ligatable, phosphorylated C-probes are circularized after the aforementioned ligation regimen. Assuming zero-mean random error and 100% C-probe competence, ligation mix was diluted to two calculated concentrations, differing by four-fold, and such that each dilution should provide at least one amplification reaction without any template molecules, when replicate reactions were performed at the designed replicate number and reaction volume.

A 2×RAM core reaction mix was created containing: 2× isothermal reaction buffer and 0.26 units/µl Bst Pol2 WS (New England Biolabs, Ipswich, Mass.), 0.4 mM each dNTP, and 0.5× Eva Green (Biotium Inc., Hayward, Calif.). Two, 2× primer-template mixtures each containing RAM Forward primer Cpr8FVFwd76_18 (5'ATGGACT-TCACGCCTACA) (SEQ ID NO: 3) at 2.4 µM; RAM reverse primer Cpr8FVRvs87_18 (5'TGTATTCCTCGCCT-GTCC) (SEQ ID NO: 4 at 2 µM; 2 µM fluorescein (BioRad, Hercules, Calif.) solution in DMSO were prepared, and each primer-template mixture was brought to final volume by addition of a template dilution prepared as described. Reaction mixtures were made by combining equal volumes of 2× core reaction mix and of one of the two 2× primer-template mixes; then, 20 µl reaction mix was aliquoted into the wells of a 96 well plate. Real-time reactions were done in an iCycler real-time instrument (BioRad, Hercules, Calif.) set to collect continuous real-time data.

---

What is claimed is:

1. A computer-implemented method for determining a value representative of an amount of a nucleic acid sequence in a sample, comprising:

performing, by a real-time amplification detection system, continuous, non-cyclic isothermal amplification of a sample comprising a nucleic acid sequence, a subsequence of the nucleic acid sequence, or a complementary sequence of the nucleic acid sequence; and a fluorescent dye;

repeatedly measuring, by the real-time amplification detection system, a signal comprising light emitted from the fluorescent dye;

recording, by the real-time amplification detection system, isothermal amplification data comprising a plurality of data points, each data point comprising (i) a measured signal; and (ii) a time that the signal was measured, wherein said recording is performed at a frequency sufficient for statistically significant biochemical reaction rate determination;

receiving, by a computer having at least one central processing unit including at least one microprocessor configured to execute instructions stored on at least one non-transitory computer-readable medium, the isothermal amplification data recorded by the by the real-time amplification detection system;

performing first processing, by the computer, of the isothermal amplification data to determine whether amplification has occurred, wherein the first processing comprises:

dividing, by the computer, the isothermal amplification data into multiple sub-segments of predetermined size;

dividing, by the computer, each sub-segment equally into proximal signal data comprising earlier data points and distal signal data comprising later data points;

determining, by the computer, a segment ratio for each sub-segment by determining a sum of the distal signal data and a sum of the proximal signal data, and dividing the sum of the distal signal data by the sum of the proximal signal data;

determining, by the computer, a maximum segment ratio, and dividing the isothermal amplification data into a baseline segment and a plateau segment separated at the position of the maximum segment ratio;

dividing, by the computer, the baseline segment and the plateau segment into proximal and distal halves, and determining a first mode comprising the statistical mode of the proximal half of the baseline segment and a second mode comprising the statistical mode of the distal half of the plateau segment;

determining reaction amplitude, comprising the difference between the first mode and the second mode;

when the amplitude is determined not to be greater than a predetermined threshold, determining, by the computer, that no amplification has occurred; and when the amplitude is determined to be greater than the predetermined threshold, determining, by the computer, that amplification has occurred;

when amplification is determined not to have occurred, ending the method;

when amplification is determined to have occurred, performing second processing, by the computer, of a logarithmic transformation of the isothermal amplification data, identifying an initial point;

performing third processing, by the computer, of the logarithmic transformation of the isothermal amplification data, selecting a current region around the initial point, and fitting a linear model to the current region;

performing fourth processing, by the computer, of the logarithmic transformation of the isothermal amplification data, determining a first correlation coefficient for the current region; extending the current region by a defined step size; determining a second correlation coefficient for the extended region; and comparing the first correlation coefficient and the second correlation coefficient;

when a difference between the first correlation coefficient and the second correlation coefficient does not exceed a set maximum, defining, by the computer, the extended region as the current region and repeating said extending;

when the difference between the first correlation coefficient and the second correlation coefficient exceeds the set maximum, defining, by the computer, the extended region as a selected data subset;

determining, by the computer, values of predefined statistical measures for the data subset, including initial and final time points delimiting the data subset, number of data points contained in the data subset, and values for predefined parameters of the model;

storing, by the computer, the data subset and the statistical measures in a database comprising at least one non-transitory computer-readable medium;

determining, by the computer, the value representative of the amount of the nucleic acid sequence in the sample based on the values for the parameters of the model; and displaying to a user, by the computer, the value representative of the amount of the nucleic acid sequence in the sample.

2. The method of claim 1, wherein the second processing comprises fitting a smoothing spline to the logarithmic transformation of the isothermal amplification data, and wherein the initial point is a first derivative maximum obtained from the fitted spline.

3. The method of claim 1, wherein the third processing comprises fitting a least-squares linear regression model to the logarithmic transformation of the isothermal amplification data, and wherein the parameters of the model include a slope and a Y-intercept of the line.

4. The method of claim 1, wherein the predetermined segment size is based on at least one of the number of data points and data variance.

5. The method of claim 1, performed in replicate on a plurality of aliquots of the sample, and further comprising:
when amplification is determined to have occurred in at least one aliquot, and not to have occurred in at least one other aliquot, determining, by the computer, a ratio of number of aliquots with no amplification to number of aliquots with amplification; and
determining, by the computer, the value representative of the amount of the nucleic acid sequence in the sample based on statistical analysis of the ratio.

6. The method of claim 1, performed in replicate on a plurality of aliquots of the sample, and further comprising:
when amplification is determined to have occurred in at least two aliquots, generating, by the computer, a tabular compilation of the values for the parameters of the model for each of the at least two aliquots, and
determining, by the computer, the value representative of the amount of the nucleic acid sequence in each of the at least two aliquots, based on statistical analysis of values in the tabular compilation.

7. The method of claim 1, performed in replicate on a plurality of aliquots of the sample, and further comprising:
determining, by the computer, the value representative of the amount of the nucleic acid sequence in the sample using values determined from all the replicates.

8. The method of claim 1, wherein the nucleic acid sequence is bound to a non-nucleic acid molecule, and further comprising:
determining, by the computer, a value representative of an amount of the non-nucleic acid molecule in the sample based on the value representative of the amount of the nucleic acid sequence in the sample.

9. The method of claim 1, wherein the isothermal amplification comprises two-primer ramified rolling circle amplification (RAM).

10. The method of claim 1, wherein the isothermal amplification comprises helicase-dependent amplification (HDA), recombinase polymerase amplification (RPA), rolling circle amplification (RCA), loop-mediated isothermal amplification (LAMP), nicking enzyme amplification reaction (NEAR), or self-sustained sequence replication (3SR).

11. The method of claim 1, performed on a plurality of samples, wherein the isothermal amplification is the same for each sample and one or more experimental factors of the isothermal amplification are systematically varied for process optimization.

* * * * *